(12) United States Patent
Zhao

(10) Patent No.: US 11,499,918 B2
(45) Date of Patent: Nov. 15, 2022

(54) CELL DETECTION METHOD AND CELL DETECTION DEVICE

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventor: Yingying Zhao, Beijing (CN)

(73) Assignees: BEIJING BOE OPTOELECTRONICS TECHNOLOGY CO., LTD., Beijing (CN); BEIJING BOE TECHNOLOGY DEVELOPMENT CO., LTD., Beijing (CN)

(*) Notice: Subject to any disclaimer, the term of this patent is extended or adjusted under 35 U.S.C. 154(b) by 301 days.

(21) Appl. No.: 16/651,581

(22) PCT Filed: Apr. 29, 2019

(86) PCT No.: PCT/CN2019/085012
§ 371 (c)(1),
(2) Date: Mar. 27, 2020

(87) PCT Pub. No.: WO2020/220205
PCT Pub. Date: Nov. 5, 2020

(65) Prior Publication Data
US 2021/0239616 A1    Aug. 5, 2021

(51) Int. Cl.
*G01N 21/64* (2006.01)
*G01N 1/30* (2006.01)
(Continued)

(52) U.S. Cl.
CPC .......... *G01N 21/6428* (2013.01); *G01N 1/30* (2013.01); *G01N 15/1429* (2013.01);
(Continued)

(58) Field of Classification Search
CPC .. G01N 21/6428; G01N 1/30; G01N 15/1429; G01N 33/49; G01N 2001/302;
(Continued)

(56) References Cited

U.S. PATENT DOCUMENTS

2017/0056887 A1     3/2017   Hadwen et al.
2019/0003953 A1*    1/2019   Kaneko ................. G01N 21/64

FOREIGN PATENT DOCUMENTS

CN    107614684 A    1/2018
CN    107923914 A    4/2018
(Continued)

*Primary Examiner* — David P Porta
*Assistant Examiner* — Meenakshi S Sahu
(74) *Attorney, Agent, or Firm* — Dilworth & Barrese, LLP.; Michael J. Musella, Esq.

(57) ABSTRACT

A cell detection method and a cell detection device. The cell detection method includes: dividing a liquid sample into a plurality of droplets in a sample detection region so that each of the plurality of droplets includes fewer than ten cells; and performing optical detection on the plurality of droplets in the sample detection region to determine a target droplet including a target cell from the plurality of droplets.

19 Claims, 6 Drawing Sheets

(51) Int. Cl.
*G01N 15/14* (2006.01)
*G01N 33/49* (2006.01)
*G01N 15/10* (2006.01)

(52) U.S. Cl.
CPC ....... *G01N 33/49* (2013.01); *G01N 2001/302* (2013.01); *G01N 2015/1006* (2013.01); *G01N 2021/6439* (2013.01)

(58) Field of Classification Search
CPC ... G01N 2015/1006; G01N 2021/6439; G01N 15/1404; G01N 2015/1415; G01N 15/1463; G01N 2015/1481; G01N 2015/1486; G01N 21/6456; G01N 2021/035; G01N 21/64
See application file for complete search history.

(56) References Cited

FOREIGN PATENT DOCUMENTS

| | | | | |
|---|---|---|---|---|
| CN | 108884486 A | | 11/2018 | |
| WO | WO 2016/168584 | * | 4/2016 | ............. C12N 15/10 |

* cited by examiner

CELL DETECTION METHOD AND CELL DETECTION DEVICE

TECHNICAL FIELD

Embodiments of the present disclosure relate to a cell detection method and a cell detection device.

BACKGROUND

The number of circulating tumor cells (CTCs) is closely related to the development and metastasis of cancer. The CTC is a general term for all tumor cells in peripheral blood, which fall off from a solid tumor focus (primary focus, metastatic focus) and enter the peripheral blood circulation spontaneously or due to diagnosis and treatment means. A large number of clinical studies have shown that tracking and monitoring the number of CTCs is helpful for early diagnosis, prognosis judgment and efficacy evaluation of cancer. However, the number of CTCs in blood is extremely small Each milliliter of blood contains about 1 billion red blood cells and 100,000 white blood cells, while the number of CTCs may be only one to a dozen or so. Therefore, in order to detect CTCs in such a large cell population and obtain an accurate cell number, we need to rely on sensitive detection technology.

SUMMARY

At least one embodiment of the present disclosure provides a cell detection method, which includes:

dividing a liquid sample into a plurality of droplets in a sample detection region so that each of the plurality of droplets includes fewer than ten cells; and performing optical detection on the plurality of droplets in the sample detection region to determine a target droplet including a target cell from the plurality of droplets.

For example, the cell detection method according to at least one embodiment of the present disclosure further includes:

calculating a number of the target droplet including the target cell, according to a result of the optical detection.

For example, in the cell detection method according to at least one embodiment of the present disclosure, the performing the optical detection on the plurality of droplets in the sample detection region to determine the target droplet including the target cell from the plurality of droplets includes:

obtaining an optical image of the sample detection region including the plurality of droplets to identify the target droplet including the target cell from the obtained optical image.

For example, the cell detection method according to at least one embodiment of the present disclosure further includes: staining the liquid sample with a fluorescent stain agent, wherein the obtaining the optical image of the sample detection region including the plurality of droplets to identify the target droplet including the target cell from the obtained optical image includes:

obtaining a bright-field image and a fluorescence image of the sample detection region including the plurality of liquid droplets;

determining at least one droplet including at least one cell in the plurality of droplets via the bright-field image; and determining the target droplet including the target cell from the at least one droplet including the at least one cell via the fluorescence image.

For example, in the cell detection method according to at least one embodiment of the present disclosure, the sample detection region includes a first drive array, and the first drive array includes first drive units distributed in an array, and the method further includes: determining coordinates of the target droplet including the target cell in the first drive array from the optical image, and collecting the target droplet including the target cell.

For example, in the cell detection method according to at least one embodiment of the present disclosure, the collecting the target droplet including the target cell includes:

planning a movement path of the target droplet including the target cell in the first drive array, and driving the target droplet including the target cell to a sample collection region via the first drive array according to the planned movement path.

For example, in the cell detection method according to at least one embodiment of the present disclosure, the fluorescent stain agent includes at least one selected from a group consisting of: a DAPI fluorescent agent, a CK-FITC fluorescent agent, and a CD45-PE fluorescent agent.

For example, in the cell detection method according to at least one embodiment of the present disclosure, the dividing the liquid sample into the plurality of droplets so that each of the plurality of droplets includes fewer than ten cells includes:

providing an electrical signal to the first drive units of the first drive array to divide the liquid sample into the plurality of droplets.

For example, the cell detection method according to at least one embodiment of the present disclosure further includes:

providing the liquid sample in a sample pretreatment region including a second drive array, wherein the second drive array includes second drive units distributed in an array; and providing an electrical signal to the second drive units of the second drive array to pretreat the liquid sample, and to drive the pretreated liquid sample into the sample detection region.

For example, in the cell detection method according to at least one embodiment of the present disclosure, the target cell includes a circulating tumor cell.

For example, in the cell detection method according to at least one embodiment of the present disclosure, the dividing the liquid sample into the plurality of droplets so that each of the plurality of droplets includes fewer than ten cells includes:

dividing the liquid sample into the plurality of droplets so that each of the plurality of droplets includes at most one cell.

At least one embodiment of the present disclosure further provides a cell detection device, which includes:

a drive substrate, the drive substrate including a sample detection region, the sample detection region including a first drive array, the first drive array including first drive units distributed in an array, the first drive units being configured to be capable of dividing a liquid sample in the sample detection region into a plurality of droplets under a control of an electrical signal so that each of the plurality of droplets includes fewer than ten cells;

an imaging unit, configured to obtain an optical image of the sample detection region including the plurality of droplets; and an analysis unit, in signal connection with the imaging unit and configured to identify a target droplet including a target cell from the obtained optical image.

For example, the cell detection device according to at least one embodiment of the present disclosure further includes: a control unit, configured to determine coordinates of the target droplet including the target cell in the first drive array from the optical image, to plan a movement path of the target droplet including the target cell in the first drive array according to the coordinates of the target droplet including the target cell in the first drive array, and to drive the target droplet including the target cell to a sample collection region via the first drive array according to the planned movement path For example, the cell detection device according to at least one embodiment of the present disclosure further includes an opposite substrate, the opposite substrate being opposite to the drive substrate to define a channel allowing a liquid sample to flow between the drive substrate and the opposite substrate.

For example, in the cell detection device according to at least one embodiment of the present disclosure, at least part of the opposite substrate is at least partially transparent, and the imaging unit is configured to obtain the optical image of the plurality of droplets through the at least part of the opposite substrate.

For example, in the cell detection device according to at least one embodiment of the present disclosure, the opposite substrate further includes a reference electrode.

For example, in the cell detection device according to at least one embodiment of the present disclosure, the analysis unit is further configured to calculate a number of the target droplet including the target cell.

For example, the cell detection device according to at least one embodiment of the present disclosure further includes a stain agent supply portion, the stain agent supply portion being configured to supply a fluorescent stain agent so that the fluorescent stain agent stains the liquid sample.

For example, in the cell detection device according to at least one embodiment of the present disclosure, the imaging unit is configured to obtain a bright-field image and a fluorescence image of the sample detection region including the plurality of droplets, and the analysis unit is configured to:

determine at least one droplet including at least one cell in the plurality of droplets via the bright-field image; and determine the target droplet including the target cell from the at least one droplet including the at least one cell via the fluorescence image.

For example, in the cell detection device according to at least one embodiment of the present disclosure, the drive substrate further includes a sample pretreatment region, the sample pretreatment region includes a second drive array, the second drive array includes second drive units distributed in an array, and the second drive array is configured to pretreat the liquid sample and to drive the pretreated liquid sample into the sample detection region under a control of an electrical signal.

For example, in the cell detection device according to at least one embodiment of the present disclosure, a size of the first drive unit in at least one direction is less than or equal to a diameter of the target cell.

For example, in the cell detection device according to at least one embodiment of the present disclosure, the first drive units are configured to be capable of dividing the liquid sample provided in the sample detection region into the plurality of droplets under a control of an electrical signal so that each of the plurality of droplets includes at most one cell.

BRIEF DESCRIPTION OF THE DRAWINGS

In order to clearly illustrate the technical solution of the embodiments of the present disclosure, the drawings of the embodiments will be briefly described in the following; it is obvious that the described drawings are only related to some embodiments of the present disclosure and thus are not limitative of the present disclosure.

DETAILED DESCRIPTION

Figure 1:
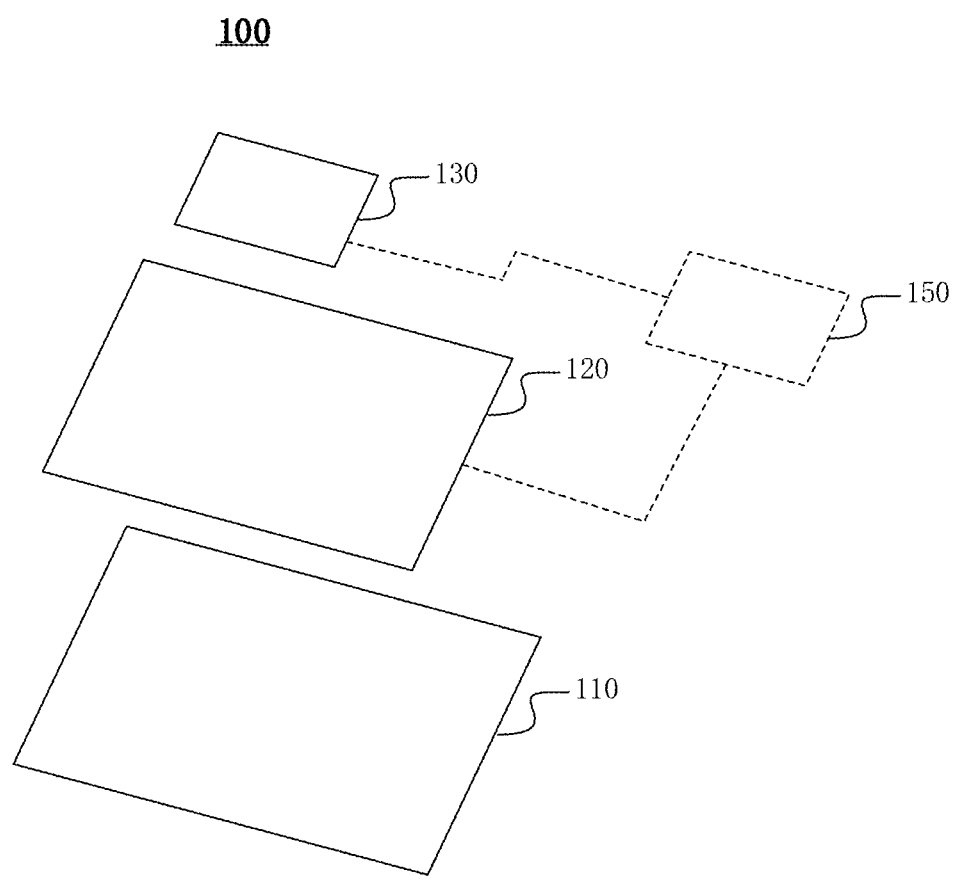
FIG. 1 is a schematic exploded view of a cell detection device according to at least some embodiments of the present disclosure.

In order to make objects, technical details and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

CTC detection is mainly divided into two aspects: CTC separation, and CTC analysis and identification.

CTC separation methods mainly include morphology-based enrichment separation and immunology-based enrichment separation. Morphology-based enrichment separation performs separation mainly based on physical differences between CTCs and other blood cells, such as size, density and surface charge, etc. However, this method has a low distinguishability for cells with the same or similar size, and is easy to cause counting errors. Immunology-based enrichment separation uses the interaction between cancer cell surface antigen and antibody conjugated to magnetic beads to form antigen-antibody-magnetic bead complexes. Under the action of an external magnetic field, the antigen-antibody-magnetic bead complexes can move and adsorb CTCs directionally so as to realize the separation and capture of cancer cells. However, the antibody of the epithelial cell adhesion molecule (Epithelial cell adhesion molecule, EpCAM) consumed by this method is expensive. Moreover, cells that do not express EpCAM cannot be captured, and the separated cells may be damaged in cell integrity and activity because magnetic beads cannot be completely separated from the cells, which may affect the reuse of the captured cells to some extent.

CTC analysis and identification methods are mainly based on counting or typing detection of specific molecular markers expressed by CTCs. Commonly used methods for CTC identification in clinical and laboratory research include immunofluorescence identification, polymerase chain reaction (PCR), fluorescence in situ hybridization (FISH) and high-throughput sequencing, etc. Most of these detection methods have low sensitivity, long detection time, low throughput and poor detection accuracy.

In addition, some CTC detection systems need to be combined with a fluorescence confocal microscope, a flow cytometer and other equipment. These CTC detection systems usually have the following problems: the required detection equipment is bulky, the supporting equipment is too expensive, and the operation is complicated; sample transfer between different chambers is easy to cause cell loss; and the separation efficiency of CTCs is low, the detection time is long and the throughput is low. These problems affect the accuracy of CTC detection and hinder the clinical promotion of CTC detection technology.

At least one embodiment of the present disclosure provides a cell detection device and a cell detection method, which do not need to be combined with equipment which is bulky, expensive and difficult to operate such as a fluorescence confocal microscope and a flow cytometer, etc., and do not cause the problem of cell loss caused by sample transfer between different chambers. In addition, the cell detection device and the cell detection method according to at least one embodiment of the present disclosure also have the characteristics of high separation efficiency, short detection time, high throughput, high detection accuracy, etc.

FIG. 1 is a schematic exploded view of a cell detection device according to some embodiments of the present disclosure. As shown in FIG. 1, the cell detection device 100 according to some embodiments of the present disclosure includes a drive substrate 110, an imaging unit 120 and an analysis unit 130.

Figure 2A:
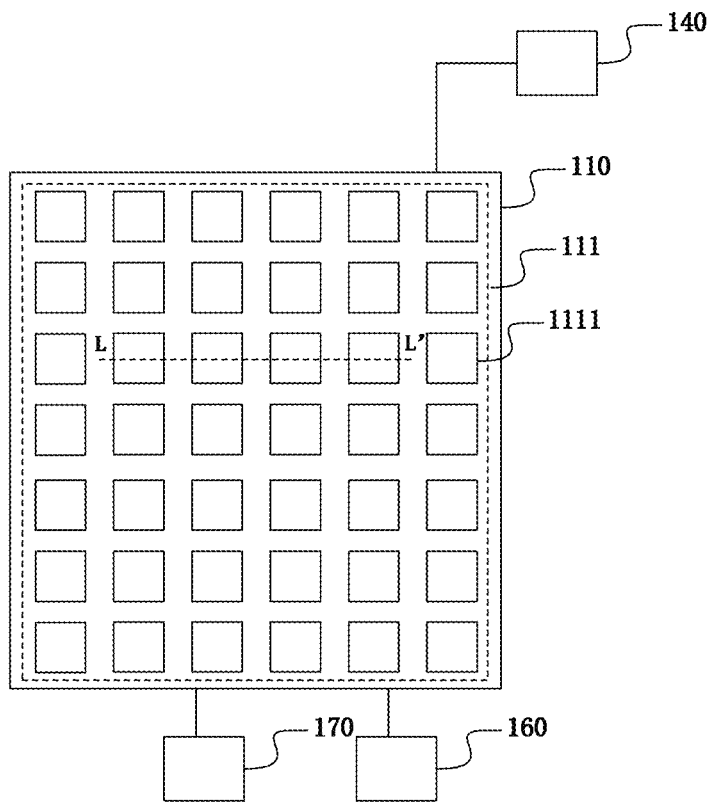
FIG. 2A is a top view of the drive substrate in FIG. 1.

FIG. 2A shows a top view of the drive substrate 110 in FIG. 1. As shown in FIG. 2A, the drive substrate 110 includes a sample detection region 111, the sample detection region 111 includes a first drive array, the first drive array includes first drive units 1111 distributed in an array, the first drive units 1111 are configured to be capable of dividing a liquid sample in the sample detection region 111 into a plurality of droplets under the control of an electrical signal so that each of the plurality of droplets includes fewer than ten cells. For example, each droplet includes 9 cells, 8 cells, 7 cells, 6 cells, 5 cells, 4 cells, 3 cells, 2 cells, 1 cell, or no cells.

The drive substrate 110 may have any suitable planar shape, such as a rectangular shape, a triangular shape, a diamond shape, a circular shape, an irregular shape, etc., and the embodiments of the present disclosure are not limited thereto. Exemplarily, in FIG. 2A, the drive substrate 110 is rectangular.

According to actual requirements, the first drive units 1111 may have any suitable planar shape, such as a rectangular shape, a triangular shape, a diamond shape, a circular shape, an irregular shape, etc. Exemplarily, in FIG. 2A, the first drive units 1111 are rectangular and distributed in 7 rows*6 columns. The distance between any two adjacent first drive units 1111 (including the distance in the row direction and the distance in the column direction) may be the same or different.

In the case where a drive signal is applied, the first drive array may drive the droplets on the upper surface of the drive substrate 110 to move along the row direction, column direction or another direction (e.g., diagonal direction) of the array, and may also perform other operations, such as splitting or fusing droplets, etc.

Figure 2B:
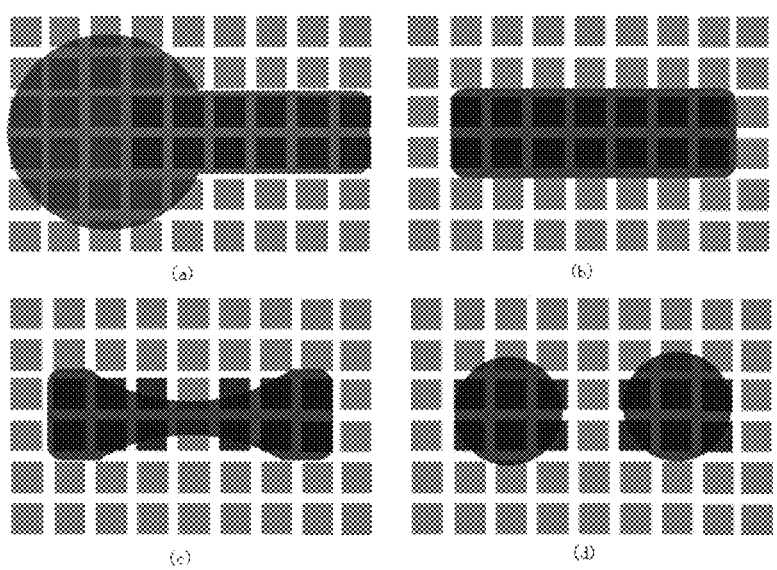
FIG. 2B is a schematic diagram of an exemplary process of splitting droplets by the drive substrate in FIG. 2A.

FIG. 2B is a schematic diagram of an exemplary process of splitting droplets by the drive substrate 110 in FIG. 2A. As shown in part (a) of FIG. 2B, by applying a drive signal to the first drive units 1111 above which the droplet is located and the first drive units 1111 in two rows at the right side of the droplet, the droplet may be elongated in the row extension direction of the two rows of first drive units 1111. As shown in part (b) of FIG. 2B, a drive signal is applied to other first drive units 1111 in the row extension direction described above, so that the droplet continues to be elongated until the droplet is elongated into a strip. As shown in part (c) of FIG. 2B, the two first drive units 1111 corresponding to the center of the elongated droplet are de-energized (i.e., no drive signal is supplied thereto), so that the droplet is of a butterfly shape. As shown in part (d) of FIG. 2B, the first drive units 1111 at the center are kept de-energized, so that the droplet may be split into two droplets under the action of surface tension. The operation process of splitting droplets by the drive substrate 110 described above is merely exemplary, and the embodiments of the present disclosure are not limited thereto.

Figure 3:
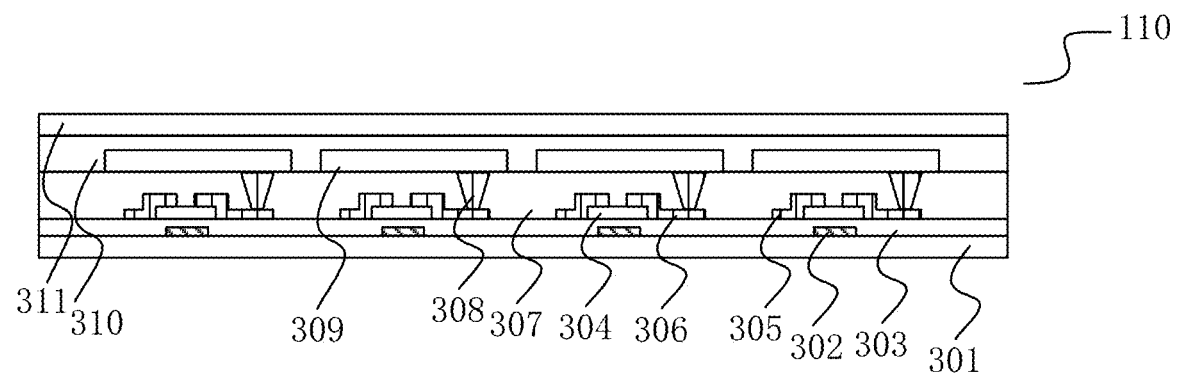
FIG. 3 is a cross-sectional view taken along line L-L' in FIG. 2A.

FIG. 3 shows a cross-sectional view taken along line L-L' in FIG. 2A. As shown in FIG. 3, the drive substrate 110 according to some embodiments of the present disclosure includes a base substrate 301. The base substrate 301 may be made of a rigid material or a flexible material. For example, the base substrate 301 may be made of glass, ceramic, silicon, polyimide, or the like. The base substrate 301 may support elements formed thereon.

The first drive units 1111 are located on the base substrate 301. The first drive units 1111 may be directly formed on the base substrate 301, or may be prepared as a separate element and then be bonded to the base substrate 301 by bonding. Each first drive unit 1111 may include a first switching element and a drive electrode 309 electrically connected to the first switching element. The drive electrode 309 performs an operation on the droplet in the case where a voltage is applied to the drive electrode 309. Each first switching element is configured to provide a drive signal to one or a plurality of drive electrodes 309. For example, the first switching elements are in one-to-one correspondence with the drive electrodes 309. As an example, in FIG. 3, the first switching element is shown in the form of a thin film transistor, however, those skilled in the art could understand that the first switching element may also be implemented in other forms, such as a field effect transistor, which is not limited in the embodiments of the present disclosure. The drive electrode 309 may be formed of any suitable material, such as metal (e.g., alloy), doped semiconductor material (e.g., polysilicon), oxide conductive material (e.g., indium tin oxide (ITO), indium zinc oxide (IZO)), etc., and the embodiments of the present disclosure are not limited thereto.

In some embodiments, the size of the first drive unit 1111 in at least one direction (e.g., may be width (e.g., rectangle), side length (e.g., square or equilateral triangle) or diameter (e.g., circle) according to the shape thereof) may be less than or equal to the diameter of the target cell. The first drive units 1111 may be configured to be capable of splitting a liquid sample in the sample detection region into a plurality of droplets under the control of an electrical signal so that each of the plurality of droplets includes at most one cell. In the case where the first drive units 1111 are configured to divide the liquid sample into droplets including at most one cell, accurate identification and operation of the droplets may be realized. For example, in an exemplary embodiment, the size of the drive electrode 309 of the first drive unit 1111 in at least one direction may be less than or equal to the diameter of the target cell.

As shown in FIG. 3, the first switching element taking a thin film transistor as an example may include a gate electrode 302, a gate insulating layer 5013, an active layer 304, a first electrode 305 and a second electrode 306. As an example, in the embodiment of the present disclosure, the first electrode 305 is a source electrode and the second electrode 306 is a drain electrode. However, in other embodiments, the first electrode 305 may be a drain electrode and the second electrode 306 may be a source electrode, which is not limited in the embodiments of the present disclosure. An insulating layer or dielectric layer 307 is formed between the drive electrode 309 and the thin film transistor. The drive electrode 309 is in electrical contact with the second electrode 306 through a via hole 308 in the insulating layer 307 to receive an electrical signal from the second electrode 306.

As shown in FIG. 3, the cell detection device 100 may not include an opposite substrate opposite to the drive substrate 110. In this case, by providing different drive voltages to adjacent drive electrodes 309, droplets exhibit different wetting degrees on the surfaces of the adjacent drive electrodes 309, so that the droplets move to the wetter side under the drive of the internal pressure difference. By changing the magnitudes, polarities, etc., of the voltages of adjacent drive electrodes 309, the moving speed and direction of droplets may be controlled.

Figure 4:
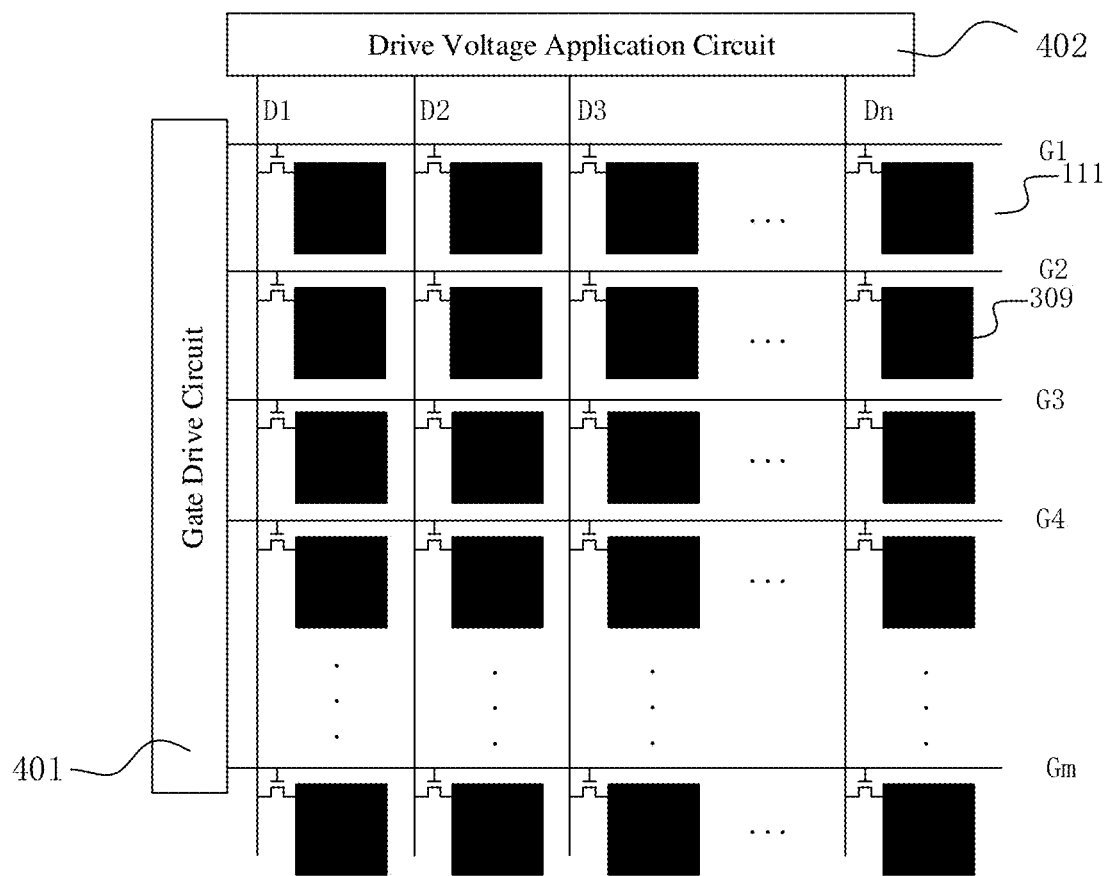
FIG. 4 is a schematic plan view of a first drive array according to at least some embodiments of the present disclosure.

FIG. 4 shows a schematic plan view of a first drive array according to some embodiments of the present disclosure. In FIG. 4, a first switching element in the form of a thin film transistor is shown, and first signal lines G1-Gm are gate lines and second signal lines D1-Dn are data lines. In the drive unit, the gate electrode 302 of the thin film transistor is electrically connected to one of the first signal lines G1-Gm, the first electrode 305 of the thin film transistor is electrically connected to one of the second signal lines D1-Dn, and the second electrode 306 of the thin film transistor is electrically connected to the drive electrode 309, so that the thin film transistor outputs a drive signal applied by the second signal line to the drive electrode 309 under the control of the first signal line.

The plurality of first signal lines G1-Gm are connected to, for example, the gate drive circuit 401, and the plurality of second signal lines D1-Dn are connected to the drive voltage application circuit 402. The gate drive circuit 401, for example, may be directly prepared on the base substrate 301, or may be prepared as a separate gate drive chip and then be bonded to the base substrate 301 by bonding. Similarly, the drive voltage application circuit 402, for example, may be directly prepared on the base substrate 301, or may be prepared as a separate drive voltage application chip and then be bonded to the base substrate 301 by bonding.

In FIGS. 3 and 4, one first switching element is electrically connected to one drive electrode 309, however, according to actual requirements, in some embodiments, a first switching element may also be electrically connected to a plurality of drive electrodes 309 so that the plurality of drive electrodes 309 may receive the same drive signal at the same time, thereby providing a greater drive force.

Referring to FIG. 3, the drive substrate 110 according to some embodiments of the present disclosure may further include a first hydrophobic layer 311, and the first hydrophobic layer 311 is formed on a surface of the drive substrate 110 for carrying droplets. The first hydrophobic layer 311 may prevent droplets from penetrating into the interior of the drive substrate 110, reduce the loss of the droplets 200, and help the droplets 200 to move on the drive substrate 110. The first hydrophobic layer 311 is located on a surface of the drive electrode 309 away from the base substrate 301. The first hydrophobic layer 311 may increase the gradient of surface tension, thereby facilitating the movement of droplets on the drive substrate 110. The first hydrophobic layer 311 may be directly formed on the surface of the drive electrode 309, or an insulating layer 310 may be further formed between the first hydrophobic layer 311 and the drive electrode 309, whereby the drive electrode 309 may be electrically insulated from the droplets. The insulating layer 310 may also function as a planarization layer, so that the drive substrate 110 has a flat surface. In some exemplary embodiments, the first hydrophobic layer 311 may be formed of a material such as teflon (teflon), Cytop® (perfluoro(1-butenylvinylether)polymer), etc., and the insulating layer 310 may be formed of an inorganic insulating material or an organic insulating material, for example, may be formed of a resin. However, the embodiments of the present disclosure are not limited thereto.

In some embodiments, channels may be formed on the surface of the first hydrophobic layer 311 carrying droplets to define a movement path of the droplets. For example, the channels may be arranged to correspond to the first drive array. For example, the channels on the surface of the first hydrophobic layer 311 carrying droplets may be in 7 rows*6 columns as in the first drive array in FIG. 2A, each row of channels may be overlapped with a row of first drive units 1111, each column of channels may be overlapped with a column of first drive units 1111, and each row of channels is in fluid communication with each column of channels. In other embodiments, the surface of the first hydrophobic layer 311 carrying droplets may also be smooth, and the embodiments of the present disclosure are not limited thereto.

Figure 5:
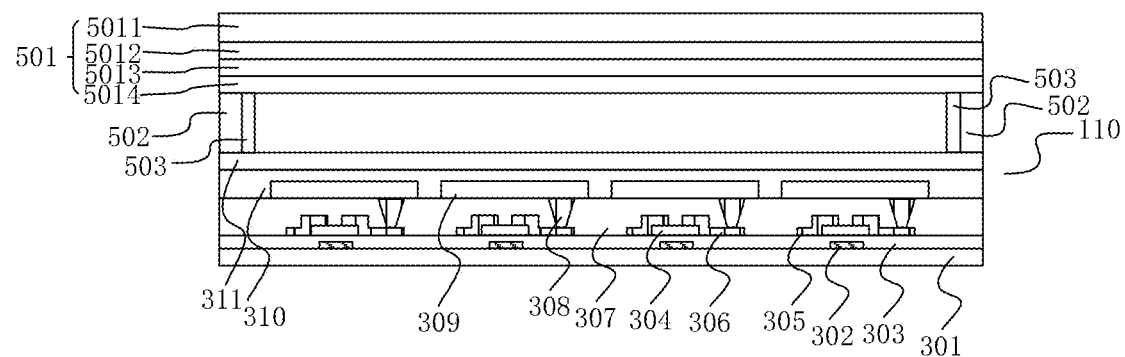
FIG. 5 is a cross-sectional view taken along line L-L' in FIG. 2A according to another embodiment of the present disclosure.

FIG. 5 shows another cross-sectional view taken along line in FIG. 2A. The cross-sectional view of the drive substrate 110 shown in FIG. 5 is basically the same as the cross-sectional view shown in FIG. 3, except that in FIG. 5, the cell detection device 100 further includes an opposite substrate 501 opposite to the drive substrate 110. The opposite substrate 501 and the drive substrate 110 are opposite and spaced apart by a certain distance to define a channel between the drive substrate 110 and the opposite substrate 501 that allows a liquid sample to flow through.

In some embodiments, the opposite substrate 501 may include a second base substrate 5011. The second base substrate 5011 may be made of a rigid material or a flexible material. For example, the second base substrate 5011 may be made of glass, ceramic, silicon, polyimide, etc. The second base substrate 5011 and the base substrate 301 may be formed of the same or different materials, which is not limited in the embodiments of the present disclosure.

In some embodiments, the opposite substrate 501 may further include a reference electrode 5012. The reference electrode 5012 is disposed on a side of the second base substrate 5011 facing the drive substrate 110. In an operation, the reference electrode 5012 may be applied with a common voltage or be grounded to form an electric field between the drive electrode 309 and the reference electrode 5012 in the operation, so as to, for example, drive droplets to move. In addition, the reference electrode 5012 may also play a role in shielding the external electromagnetic field. The reference electrode 5012 may be a planar electrode, a slit electrode, or a plurality of block electrodes connected together.

The opposite substrate 501 may further include a second insulating layer 5013 located on a side of the reference electrode 5012 facing the drive substrate 110, so that the reference electrode 5012 is insulated from droplets located between the drive substrate 110 and the opposite substrate 501. The opposite substrate 501 may further include a second hydrophobic layer 5014 located on a side of the insulating layer 5013 facing the drive substrate 110, so as to prevent droplets between the drive substrate 110 and the opposite substrate 501 from penetrating into the second insulating layer 5013, the reference electrode 5012 and/or the second base substrate 5011, reduce the loss of the droplets 200, and increase the gradient of surface tension, thereby facilitating the movement of droplets between the drive substrate 110 and the opposite substrate 501. In some exemplary embodiments, the second hydrophobic layer 5014 may be formed of a material such as teflon (teflon), Cytop® (perfluoro(1-butenylvinylether)polymer), etc., the second insulating layer 5013 may be formed of an inorganic insulating material or an organic insulating material, for example, may be formed of a resin, and the reference electrode 5012 may be formed of any suitable material such as metal, alloy, indium tin oxide (ITO), indium zinc oxide (IZO), etc. The embodiments of the present disclosure are not limited thereto. Those skilled in the art could understand that in some embodiments, the opposite substrate 501 may not include the reference electrode 5012 and the second insulating layer 5013, but only include the second base substrate 5011 and the second hydrophobic layer 5014 or only include the second hydrophobic layer 5014, and the embodiments of the present disclosure are not limited thereto.

In the cell detection device 100 according to some embodiments of the present disclosure, an adhesive (e.g., frame sealant, etc.) 502 may be used to adhere the drive substrate 110 and the opposite substrate 501 to form a cell in which droplets may move. In some embodiments, one or a plurality of spacers 503 may be formed between the drive substrate 110 and the opposite substrate 501 to define a channel for droplets to move through. At the same time, the spacers 503 may also function to maintain the distance between the drive substrate 110 and the opposite substrate 501. The spacers 503 may be formed of, for example, a resin (e.g., a photosensitive resin) or the like, and may be formed into a columnar shape or a strip dam shape or the like.

In some embodiments, the imaging unit 120 may be located above the drive substrate 110 to obtain an optical image of the sample detection region 111. In the case where the cell detection device 100 includes the opposite substrate 501, at least part of the opposite substrate 501 is at least partially transparent, so that the imaging unit 120 may obtain the optical image of the sample detection region 111 through the at least part of the opposite substrate 501 which is at least partially transparent. For example, the part of the opposite substrate 501 located in an optical path from the drive substrate 110 to the imaging unit 120 is at least partially transparent. The part of the opposite substrate 501 which is at least partially transparent may have a transmittance of, for example, 100%, 90%, 80%, 70%, 60%, 50%, 40%, 30%, 20%, 10%, or 5%, and the embodiments of the present disclosure are not limited thereto.

In some embodiments, the imaging unit 120 may be located just above the drive substrate 110, or the imaging unit 120 may be located at other locations and light is guided from the drive substrate 110 to the imaging unit 120 via a light guiding element (such as a lens, a reflector, a refractor, a transflective mirror, a filter, etc.), and the embodiments of the present disclosure are not limited thereto.

In some embodiments, the imaging unit 120 may include a light source and a photosensitive element. The light emitted from the light source of the imaging unit 120 is reflected by the drive substrate 110 and the droplets on the drive substrate 110 and then received by the photosensitive element, thereby obtaining an optical image of the sample detection region 111 including the droplets. The light source may provide, for example, visible light, ultraviolet light, infrared light, X-rays, etc. It could be understood that in some embodiments, the light source may also be a separately provided element and not included in the imaging unit 120, and the embodiments of the present disclosure are not limited thereto. The photosensitive element may be, for example, a charge coupled device (CCD), a complementary metal oxide semiconductor (CMOS) device, or the like. The photosensitive element may sense, for example, visible light, ultraviolet light, infrared light, X-ray, etc., and the embodiments of the present disclosure are not limited thereto. In some embodiments, the imaging unit 120 may include one or more kinds of photosensitive elements, wherein each kind of photosensitive elements may sense one or more selected from the group consisting of visible light, ultraviolet light, infrared light and X-ray. For example, the imaging unit 120 may obtain at least one selected from the group consisting of a visible light image of the sample detection region 111 including droplets, an ultraviolet light image (e.g., a fluorescence image) of the sample detection region 111 including droplets, an infrared light image of the sample detection region 111 including droplets and an X-ray image (e.g., a fluorescence image) of the sample detection region 111 including droplets.

According to actual requirements, the imaging unit 120 may further include a light guiding element, such as a lens, a reflector, a refractor, a transflective mirror, a filter, etc., to guide light entering the imaging unit 120 to the photosensitive element.

The imaging unit 120 may be controlled to obtain an optical image of the sample detection region 111 including droplets in real time or periodically, or the imaging unit 120 may be controlled to obtain an optical image of the sample detection region 111 including droplets. In some embodiments, the imaging unit 120 may cooperate with the first drive array of the drive substrate 110 to obtain an optical image of a preset region of the sample detection region 111 including droplets when the droplets are driven to the preset region of the sample detection region 111 by the first drive array.

Referring to FIG. 2A, in some embodiments, the cell detection device 100 may further include a stain agent supply portion 140. The stain agent supply portion 140 is configured to supply a stain agent so that the stain agent stains the liquid sample on the drive substrate 110. The stain agent supply portion 140 may be in fluid communication with the drive substrate 110, so that the stain agent from the stain agent supply portion 140 may be mixed with the liquid sample on the drive substrate 110.

In some embodiments, the stain agent supply portion 140 may adopt various methods such as a fluid drive method, a mechanical drive method, etc., and may include a device such as a pump, a push rod, etc., so as to convey the stain agent stored in the stain agent supply portion 140 or the stain agent supplied by an external stain agent source to the drive substrate 110. The stain agent supplied by the stain agent supply portion 140 may also be moved under the drive of the first drive array. In some embodiments, an output end of the stain agent supply portion 140 may be in fluid communication with the channel in the first hydrophobic layer 311 of the drive substrate 110 to enable the stain agent supplied by the stain agent supply portion 140 to move along the channel.

According to different applications, the stain agent supplied by the stain agent supply portion 140 may be, for example, a fluorescent stain agent such as 4',6-diamidino-2-phenylindole (DAPI), cytokeratin-fluorescein isothiocyanate (CK-FITC), CD45-phycoerythrin (PE), etc. DAPI may stain nuclei and emit blue fluorescence upon being excited, CK-FITC may stain cell surface proteins and emit green fluorescence upon being excited, and CD45-PE may stain leukocyte surface proteins and emit red fluorescence upon being excited. However, it could be understood that the stain agent supplied by the stain agent supply portion 140 may also include any other suitable stain agent according to the characteristics of the target cell, which is not limited in the embodiments of the present disclosure.

In some embodiments, the stain agent supply portion 140 may include a plurality of sub-stain agent supply portions, each of which is configured to supply any one of the above stain agents, such as DPAI, CK-FITC, or CD45-PE. In other embodiments, the stain agent supply portion 140 may include a single sub-stain supply portion, wherein the sub-stain agent supply portion is configured to supply a plurality of stain agents in a time-sharing manner, and the stain agent may be any one of the stain agents described above, such as DPAI, FITC, or PE.

However, it could be understood that in the case where the cell detection device 100 does not include the stain agent supply portion 140, in these embodiments, the droplets may be mixed with the stain agent in advance and then provided to the drive substrate 110.

In some embodiments, the analysis unit 130 may be in signal connection with the imaging unit 120 and configured to identify a target droplet including a target cell from an optical image obtained by the imaging unit 120. For example, the analysis unit 130 may be configured to determine droplets including a cell(s) via a bright-field image (i.e., visible light image) of the sample detection region 111 including a plurality of droplets which is acquired by the imaging unit 120, and determine a target droplet including a target cell from the droplets including the cell(s) via a fluorescence image of the sample detection region 111 including the plurality of droplets which is acquired by the imaging unit 120.

Figure 6:
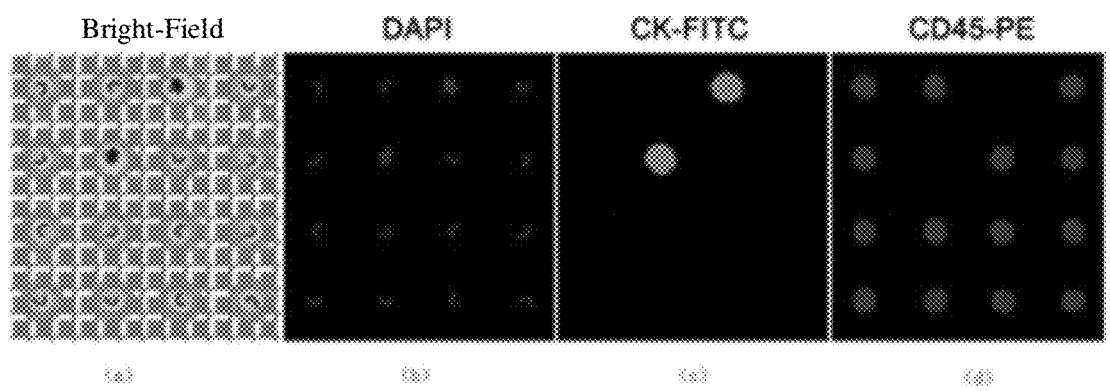
FIG. 6 is an example of an optical pattern according to at least some embodiments of the present disclosure.

In some embodiments, the above fluorescence image may include, for example, at least one selected from the group consisting of a DAPI fluorescence image, a CK-FITC fluorescence image and a CD45-PE fluorescence image. FIGS. 6(*a*)-6(*d*) are respectively a bright-field image, a DAPI fluorescence image, a CK-FITC fluorescence image and a CD45-PE fluorescence image of the sample detection region 111 including the plurality of droplets according to some embodiments of the present disclosure.

Hereinafter, the operation of the analysis unit 130 according to some embodiments of the present disclosure will be described by taking the case that the above-mentioned target cell is a circulating tumor cell (CTC) and the liquid sample is a blood sample as an example.

Figure 7:
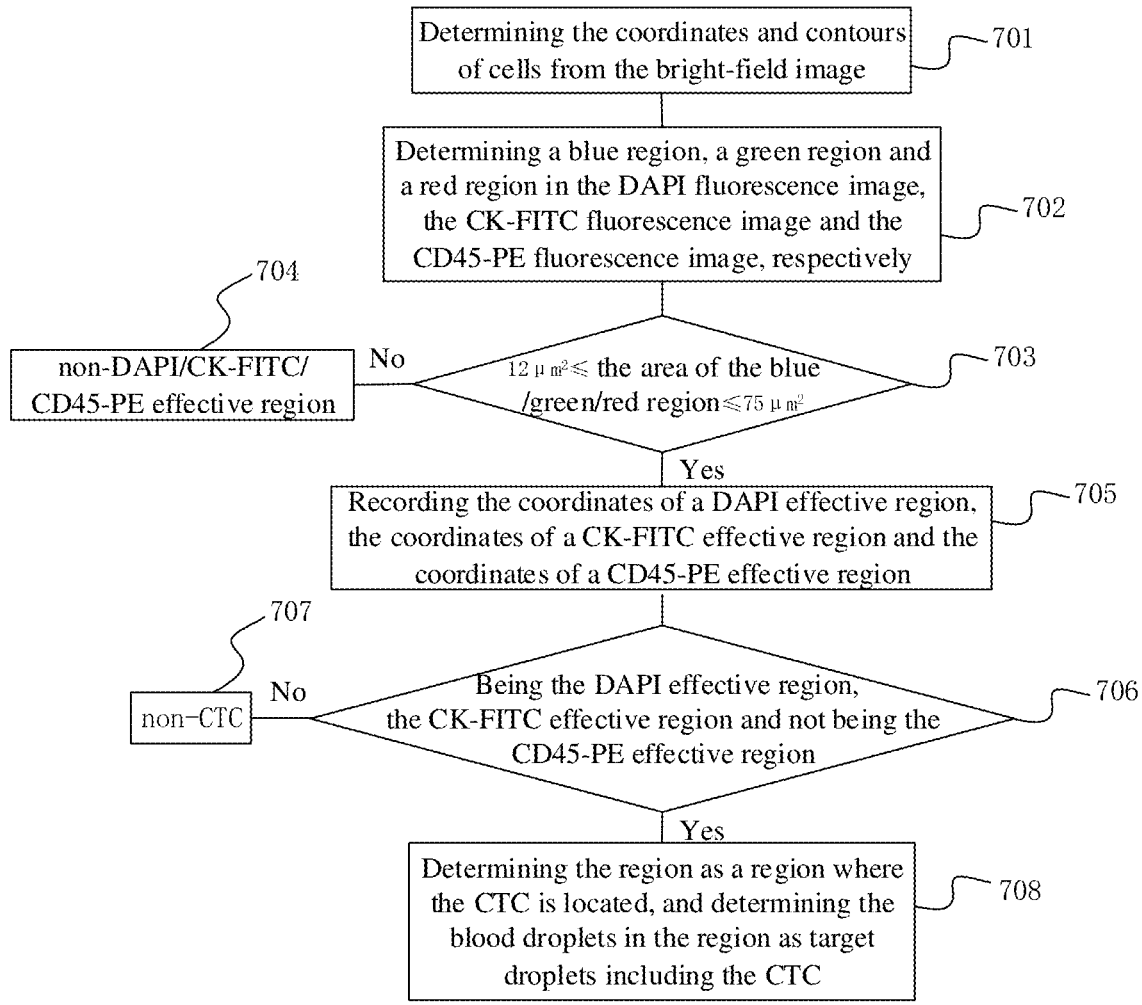
FIG. 7 is a schematic flow chart of an operation of an analysis unit according to at least some embodiments of the present disclosure.

As shown in FIG. 7, in some embodiments, the analysis unit 130 may perform the following steps S701-S708 on the bright-field image, the DAPI fluorescence image, the CK-FITC fluorescence image and the CD45-PE fluorescence image shown in FIGS. 6(*a*)-6(*d*) to determine the coordinates of the target cell. The method is specifically described as follows.

S701: determining the coordinates and contours of cells in the blood droplets from the bright-field image;

S702: determining a blue region, a green region and a red region in the DAPI fluorescence image, the CK-FITC fluorescence image and the CD45-PE fluorescence image, respectively.

S703: determining whether the area of the blue region, the area of the green region and the area of the red region are within the range of 12 $\mu m^2$ to 75 $\mu m^2$;

S704: if the area of the blue region, the area of the green area and the area of the red region are not within the above range, determining the corresponding region to be a non-DAPI effective region, a non-CK-FITC effective region or a non-CD45-PE effective region;

S705: if the area of the blue region, the area of the green area and the area of the red region are within the above-mentioned range, determining the corresponding region to be a DAPI effective region, a CK-FITC effective region or a CD45-PE effective region;

S706: Determining whether a region meets the conditions of the DAPI effective region, the CK-FITC effective region and the non-CD45-PE effective region;

S707: if the region does not meet the above conditions, determining the region as a region where the CTC(s) is not located, and determining the blood droplets in the region as non-target droplets that do not include CTC(s); and S708: if the region meets the above conditions, determining the region as a region where the CTC(s) is located, and determining the blood droplets in the region as target droplets including the CTC(s).

It could be understood that the analysis unit 130 may adopt any suitable method or algorithm to determine the contours of the cells, the blue region, the green region, the red region and the area of the region in the image, which is not limited in the embodiments of the present disclosure.

In some embodiments, the analysis unit 130 may also be configured to calculate the number of the target droplet(s) including the target cell(s). The analysis unit 130 may store the number of the target droplet(s) in a memory of the cell detection device 100 or output it to other devices connected thereto. For example, in some embodiments, in the case where the analysis unit 130 calculates the number of the CTC(s), the number of the CTC(s) may be used for early diagnosis, prognosis judgment, efficacy evaluation, etc. of cancer.

It could be understood that the analysis unit described above may be implemented in hardware, software, firmware or any combination thereof, which is not limited in the embodiments of the present disclosure.

Referring to FIG. 1, in some embodiments, the cell detection device 100 may further include a control unit 150. The control unit 150 may be in signal connection with the analysis unit 130 and the drive substrate 110. The control unit 150 may be configured to determine the coordinates of the target droplet including the target cell(s) in the first drive array from the optical image of the sample detection region 111 including droplets. For example, the control unit 150 may determine the coordinates of the target droplet including the CTC(s) determined by the analysis unit 130 in the first drive array.

In the above embodiments, the row number and column number where the first drive unit 1111 is located may be used as the coordinates of the droplet located at the first drive unit 1111 in the first drive array. For example, the coordinates of the droplet located substantially at the first drive unit 1111 in the M-th row and N-th column in the first drive array may be determined as (M, N). However, it could be understood that the embodiments of the present disclosure are not limited thereto.

In some embodiments, the control unit 150 may be further configured to plan a movement path of the target droplet including the target cell(s) in the first drive array according to the coordinates of the target droplet including the target cell(s) in the first drive array, and to drive the target droplet including the target cell(s) to a sample collection region via the first drive array according to the planned movement path. In addition, the control unit 150 may be further configured to plan a movement path of a non-target droplet that does not include the target cell in the first drive array according to the coordinates of the non-target droplet that does not include the target cell in the first drive array, and to drive the non-target droplet that does not include the target cell to a non-target liquid collection region via the first drive array according to the planned movement path. For example, referring to FIG. 2A, the drive substrate 110 may further include a sample collection region 160 and a non-target liquid collection region 170. Both the sample collection region 160 and the non-target liquid collection region 170 may be provided with grooves located outside the sample detection region 111 and in fluid communication with the sample detection region 111, which is not limited in the embodiments of the present disclosure. In addition, it could be understood that the number of the sample collection regions 160 and the number of the non-target liquid collection regions 170 shown in FIG. 2A is merely exemplary, and the embodiments of the present disclosure are not limited thereto.

It could be understood that the control unit described above may be implemented in hardware, software, firmware or any combination thereof, which is not limited in the embodiments of the present disclosure.

Figure 8:
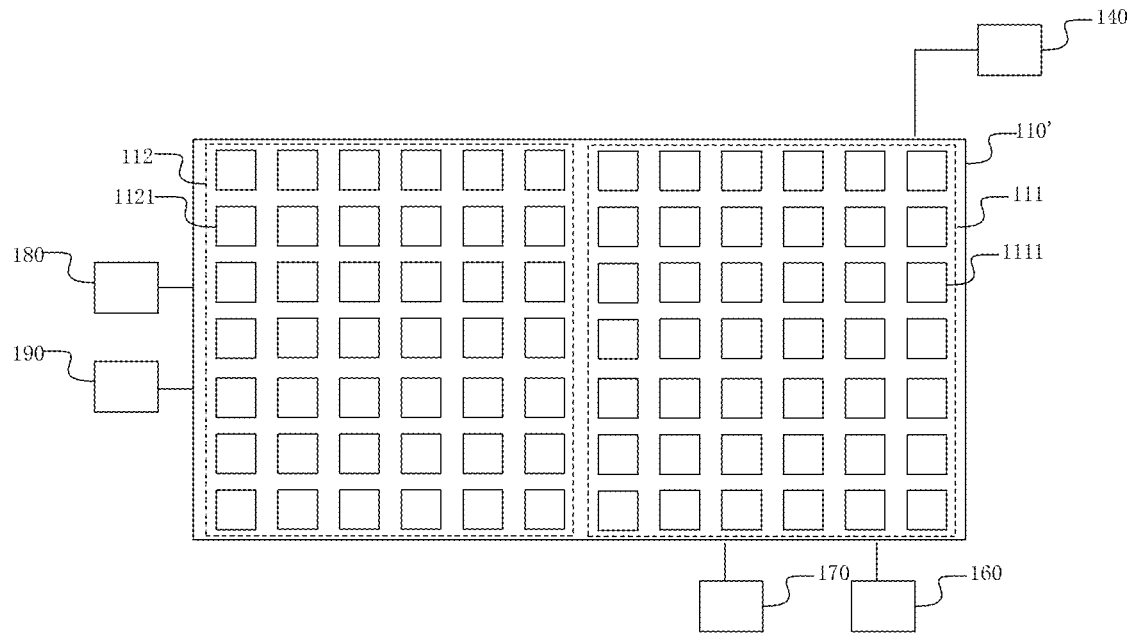
FIG. 8 is a top view of a drive substrate according to at least some embodiments of the present disclosure.

As shown in FIG. 8, the drive substrate 110' according to some embodiments of the present disclosure may further include a sample pretreatment region 112. The sample pretreatment region 112 may include a second drive array which may include second drive units 1121 distributed in an array. The second drive array is configured to be capable of pretreating a liquid sample and driving the pretreated liquid sample into the sample detection region 111 under the control of an electrical signal. For example, the second driving units 1121 may have the same structure as the first driving units 1111, and details will not be repeated in the present disclosure. In the case where the second driving units 1121 and the first driving units 1111 have the same structure, the manufacturing process may be simplified and the manufacturing costs may be reduced.

The sample pretreatment region 112 may be in fluid communication with the sample detection region 111. For example, the sample pretreatment region 112 may be formed on the same base substrate as the sample detection region 111. In the case where the drive substrate includes the sample pretreatment region and the sample detection region, the pretreatment and the detection may be synchronously carried out, so continuous detection may be realized, and detection efficiency may be improved.

It could be understood that the positional relationship between the sample pretreatment region 112 and the sample detection region 111 shown in FIG. 8 and the arrangement manner of the second drive units 1121 are merely exemplary, and the embodiments of the present disclosure are not limited thereto.

In some embodiments, the drive substrate 110' may further include a liquid sample supply portion 180 and a pretreatment solution supply portion 190. The liquid sample supply portion 180 and the pretreatment solution supply portion 190 are in fluid communication with the sample pretreatment region 112. The liquid sample supply portion 180 is configured to supply a liquid sample (e.g., a blood sample, etc.) to the sample pretreatment region 112. The pretreatment solution supply portion 190 is configured to supply one or a plurality of kinds of pretreatment solutions (e.g., red blood cell lysate, diluent, etc.) to the sample pretreatment region 112. In the sample pretreatment region 112, operations such as mixing, droplet generation, splitting, fusing, etc., may be performed on the liquid sample supplied by the liquid sample supply portion 180 and the pretreatment solution supplied by the pretreatment solution supply portion 190 under the drive of the second drive array, thereby realizing pretreatment of the liquid sample, such as dilution of blood sample, red cell lysis, fluorescence staining incubation, etc.

Similarly, the liquid sample supply portion 180 may adopt various methods such as a fluid drive method, a mechanical drive method, etc., and may include a device such as a pump, a push rod, etc., so as to convey the liquid sample stored in the liquid sample supply portion 180 or the liquid sample supplied by an external liquid sample source to the drive substrate 110. In some embodiments, an output end of the liquid sample supply portion 180 may be in fluid communication with the channel in the first hydrophobic layer 311 of the drive substrate 110 to enable the liquid sample supplied by the liquid sample supply portion 180 to move along the channel. Similarly, the pretreatment solution supply portion 190 may include a device such as a pump, a push rod, etc., so as to convey the pretreatment solution stored in the pretreatment solution supply portion 190 or the pretreatment solution supplied by an external pretreatment solution source to the drive substrate 110. In some embodiments, an output end of the pretreatment solution supply portion 190 may be in fluid communication with the channel in the first hydrophobic layer 311 of the drive substrate 110 to enable the pretreatment solution supplied by the pretreatment solution supply portion 190 to move along the channel.

The cell detection device according to the embodiments of the present disclosure does not need to be combined with equipment which is bulky, expensive and difficult to operate, such as a fluorescence confocal microscope, a flow cytometer, etc., and does not have the problem of cell loss caused by sample transfer between different chambers. In addition, the cell detection device according to the embodiments of the present disclosure also has the characteristics of high CTC separation efficiency, short detection time, high throughput, high detection accuracy, etc., when being used for CTC detection, and is suitable for clinical popularization of CTC detection technology.

Figure 9:
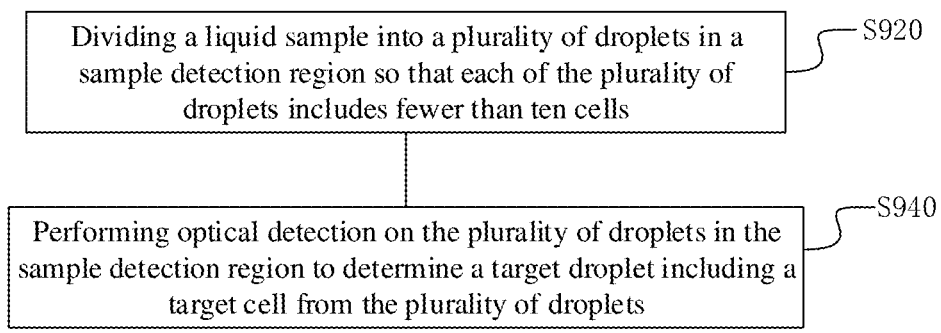
FIG. 9 is a schematic flow chart of a cell detection method according to at least some embodiments of the present disclosure.

As shown in FIG. 9, at least one embodiment of the present disclosure further provides a cell detection method 900, and the cell detection method 900 may be implemented, for example, by the cell detection device 100 described above. The cell detection method 900 according to some embodiments of the present disclosure may include:

S920: dividing a liquid sample into a plurality of droplets in a sample detection region so that each of the plurality of droplets includes fewer than ten cells; and S940: performing optical detection on the plurality of droplets in the sample detection region to determine a target droplet including a target cell from the plurality of droplets.

In some embodiments, step S920 may include: dividing the liquid sample into the plurality of droplets so that each of the plurality of droplets includes, for example, 9 cells, 8 cells, 7 cells, 6 cells, 5 cells, 4 cells, 3 cells, 2 cells, 1 cell, or no cells. In an exemplary embodiment, step S920 may include: dividing the liquid sample into the plurality of droplets so that each of the plurality of droplets includes at most one cell.

In some embodiments, the sample detection region described above may include a first drive array, and the first drive array includes first drive units distributed in an array. Step S920 may include dividing the liquid sample in the sample detection region into the plurality of droplets by supplying an electrical signal to the first drive units of the first drive array. In some embodiments, the first drive units are capable of causing each of the plurality of droplets to include fewer than ten cells under the control of the electrical signal. For example, each droplet includes 9 cells, 8 cells, 7 cells, 6 cells, 5 cells, 4 cells, 3 cells, 2 cells, 1 cell, or no cells.

In some embodiments, step S940 may include obtaining an optical image of the sample detection region including the plurality of droplets to identify the target droplet including the target cell from the obtained optical image. In some other embodiments, according to the characteristics of the liquid sample being detected and the target cell, step S940 may further include obtaining an X-ray diffraction image of the sample detection region including the droplets by irradiating the droplets in the sample detection region with X-rays. It could be understood that what is described above is merely an example of optical detection, and the embodiments of the present disclosure are not limited thereto.

In some embodiments, before step S940, the cell detection method 900 may further include staining the liquid sample with a fluorescent stain agent. The fluorescent stain agent may include, for example, at least one selected from the group consisting of DAPI, CK-FITC, and CD45-PE.

The above-mentioned step of obtaining the optical image of the sample detection region including the plurality of droplets to identify the target droplet including the target cell from the obtained optical image may include:

obtaining a bright-field image and a fluorescence image of the sample detection region including the plurality of liquid droplets;

determining the droplet including a cell(s) in the plurality of droplets via the bright-field image; and determining the target droplet including the target cell(s) from the droplet including the cell(s) via the fluorescence image.

For example, in the above-mentioned exemplary embodiment where the target cell is a circulating tumor cell (CTC) and the liquid sample is a blood sample, the above-mentioned step of obtaining the optical image of the sample detection region including the plurality of droplets to identify the target droplet including the target cell(s) from the obtained optical image may be implemented with reference to steps S701 to S708 in FIG. 7, and details will not be repeated in the present disclosure.

In some embodiments, the cell detection method 900 may further include determining coordinates of the target droplet including the target cell(s) in the first drive array from the optical image and collecting the target droplet including the target cell(s).

In the above embodiments, the row number and column number where the first drive unit is located may be used as the coordinates of the droplet located at the first drive unit in the first drive array. For example, the coordinates of the droplet located substantially at the first drive unit in the M-th row and N-th column in the first drive array may be determined as (M, N). However, it could be understood that the embodiments of the present disclosure are not limited thereto.

The above-mentioned step of collecting the target droplet including the target cell(s) may include planning a movement path of the target droplet including the target cell(s) in the first drive array, and driving the target droplet including the target cell(s) to a sample collection region via the first drive array according to the planned movement path. In some other embodiments, the cell detection method 900 may further include planning a movement path of a non-target droplet that does not include the target cell in the first drive array according to the coordinates of the non-target droplet that does not include the target cell in the first drive array, and driving the non-target droplet that does not include the target cell to a non-target liquid collection region via the first drive array according to the planned movement path.

In some embodiments, the cell detection method 900 may further include:

providing the liquid sample in a sample pretreatment region including a second drive array which includes second drive units distributed in an array; and providing an electrical signal to the second drive units of the second drive array to pretreat the liquid sample, and to drive the pretreated liquid sample into the sample detection region.

In some embodiments, according to actual requirements, the pretreatment of the liquid sample may include, for example, dilution of the blood sample, lysis of red blood cells, fluorescence staining incubation, etc. However, it could be understood that the embodiments of the present disclosure are not limited thereto.

The sample pretreatment region may be in fluid communication with the sample detection region. For example, the sample pretreatment region may be formed on the same base substrate as the sample detection region.

For example, the second drive units may have the same structure as the first drive units, thereby simplifying the manufacturing process and reducing the manufacturing costs.

In some embodiments, the cell detection method 900 may further include calculating the number of the target droplet including the target cell(s) according to the result of the optical detection. The calculated number of the target droplet including the target cell(s) may be stored in a memory or be outputted to other connected devices. In the case where the target cell is the CTC, the calculated number of the target droplet including the CTC(s) may be used for early diagnosis, prognosis judgment, efficacy evaluation, etc., of cancer.

In the cell detection method according to the embodiments of the present disclosure, there is no need to use equipment which is bulky, expensive and difficult to operate, such as a fluorescence confocal microscope and a flow cytometer, etc., and the problem of cell loss caused by sample transfer between different chambers does not exist. In addition, the cell detection method according to the embodiments of the present disclosure also has the characteristics of high CTC separation efficiency, short detection time, high throughput, high detection accuracy, etc., when being used for CTC detection, and is suitable for clinical popularization of CTC detection technology.

The foregoing merely are exemplary embodiments of the disclosure, and not intended to define the scope of the disclosure, and the scope of the disclosure is determined by the appended claims.

What is claimed is:

1. A cell detection method, comprising:
dividing a liquid sample into a plurality of droplets in a sample detection region so that each of the plurality of droplets comprises fewer than ten cells; and
performing optical detection on the plurality of droplets in the sample detection region to determine a target droplet comprising a target cell from the plurality of droplets;
wherein the sample detection region comprises a first drive array, and the first drive array comprises first drive units distributed in an array, and the first drive array is configured to drive the droplets in the sample detection region that overlap the first drive array in a direction perpendicular to a surface of the sample detection region to move; and
the dividing the liquid sample into the plurality of droplets so that each of the plurality of droplets comprises fewer than ten cells comprises:
providing an electrical signal to the first drive units of the first drive array to divide the liquid sample into the plurality of droplets so that each of the plurality of droplets comprises fewer than ten cells.

2. The method according to claim 1, further comprising: calculating a number of the target droplet comprising the target cell, according to a result of the optical detection.

3. The method according to claim 1, wherein the performing the optical detection on the plurality of droplets in the sample detection region to determine the target droplet comprising the target cell from the plurality of droplets comprises:
obtaining an optical image of the sample detection region comprising the plurality of droplets to identify the target droplet comprising the target cell from the obtained optical image.

4. The method according to claim 3, further comprising: staining the liquid sample with a fluorescent stain agent,
wherein the obtaining the optical image of the sample detection region comprising the plurality of droplets to identify the target droplet comprising the target cell from the obtained optical image comprises:
obtaining a bright-field image and a fluorescence image of the sample detection region comprising the plurality of liquid droplets;
determining at least one droplet comprising at least one cell in the plurality of droplets via the bright-field image; and
determining the target droplet comprising the target cell from the at least one droplet comprising the at least one cell via the fluorescence image.

5. The method according to claim 1, wherein
the method further comprises: determining coordinates of the target droplet comprising the target cell in the first drive array from the optical image, and collecting the target droplet comprising the target cell.

6. The method according to claim 5, wherein the collecting the target droplet comprising the target cell comprises:
planning a movement path of the target droplet comprising the target cell in the first drive array, and
driving the target droplet comprising the target cell to a sample collection region via the first drive array according to the planned movement path.

7. The method according to claim 4, wherein the fluorescent stain agent comprises at least one selected from a group consisting of: a DAPI fluorescent agent, a CK-FITC fluorescent agent, and a CD45-PE fluorescent agent.

8. The method according to claim 1, further comprising:
providing the liquid sample in a sample pretreatment region comprising a second drive array, wherein the second drive array comprises second drive units distributed in an array; and
providing an electrical signal to the second drive units of the second drive array to pretreat the liquid sample, and to drive the pretreated liquid sample into the sample detection region.

9. The method according to claim 1, wherein the target cell comprises a circulating tumor cell.

10. The method according to claim 1, wherein the dividing the liquid sample into the plurality of droplets so that each of the plurality of droplets comprises fewer than ten cells comprises:
dividing the liquid sample into the plurality of droplets so that each of the plurality of droplets comprises at most one cell.

11. A cell detection device, comprising:
a drive substrate, the drive substrate comprising a sample detection region, the sample detection region comprising a first drive array, the first drive array is configured to drive the droplets in the sample detection region that overlap the first drive array in a direction perpendicular to a surface of the sample detection region to move, the first drive array comprising first drive units distributed in an array, the first drive units being configured to be capable of dividing a liquid sample in the sample detection region into a plurality of droplets under a control of an electrical signal so that each of the plurality of droplets comprises fewer than ten cells;

an imaging unit, configured to obtain an optical image of the sample detection region comprising the plurality of droplets; and an analysis unit, in signal connection with the imaging unit and configured to identify a target droplet comprising a target cell from the obtained optical image.

12. The cell detection device according to claim 11, further comprising: a control unit, configured to determine coordinates of the target droplet comprising the target cell in the first drive array from the optical image, to plan a movement path of the target droplet comprising the target cell in the first drive array according to the coordinates of the target droplet comprising the target cell in the first drive array, and to drive the target droplet comprising the target cell to a sample collection region via the first drive array according to the planned movement path.

13. The cell detection device according to claim 11, further comprising an opposite substrate, the opposite substrate being opposite to the drive substrate to define a channel allowing a liquid sample to flow between the drive substrate and the opposite substrate.

14. The cell detection device according to claim 13, wherein at least part of the opposite substrate is at least partially transparent, and the imaging unit is configured to obtain the optical image of the plurality of droplets through the at least part of the opposite substrate.

15. The cell detection device according to claim 11, wherein the analysis unit is further configured to calculate a number of the target droplet comprising the target cell.

16. The cell detection device according to claim 11, further comprising a stain agent supply portion, the stain agent supply portion being configured to supply a fluorescent stain agent so that the fluorescent stain agent stains the liquid sample.

17. The cell detection device according to claim 16, wherein the imaging unit is configured to obtain a bright-field image and a fluorescence image of the sample detection region comprising the plurality of droplets, and the analysis unit is configured to:

determine at least one droplet comprising at least one cell in the plurality of droplets via the bright-field image; and determine the target droplet comprising the target cell from the at least one droplet comprising the at least one cell via the fluorescence image.

18. The cell detection device according to claim 11, wherein the drive substrate further comprises a sample pretreatment region, the sample pretreatment region comprises a second drive array, the second drive array comprises second drive units distributed in an array, and the second drive array is configured to pretreat the liquid sample and to drive the pretreated liquid sample into the sample detection region under a control of an electrical signal.

19. The cell detection device according to claim 11, wherein a size of the first drive unit in at least one direction is less than or equal to a diameter of the target cell, and the first drive units are configured to be capable of dividing the liquid sample provided in the sample detection region into the plurality of droplets under a control of an electrical signal so that each of the plurality of droplets comprises at most one cell.

* * * * *